United States Patent [19]
Gray et al.

[11] 4,257,911
[45] Mar. 24, 1981

[54] LIQUID CRYSTAL MATERIALS

[75] Inventors: George W. Gray, Cottingham; Damien G. McDonnell, Hull, both of England

[73] Assignee: The Secretary of State for Defence in Her Britannic Majesty's Government of the United Kingdom of Great Britain and Northern Ireland, London, England

[21] Appl. No.: 61,243

[22] Filed: Jul. 27, 1979

Related U.S. Application Data

[63] Continuation of Ser. No. 948,774, Oct. 5, 1978, abandoned, which is a continuation of Ser. No. 822,342, Aug. 5, 1977, abandoned.

[51] Int. Cl.$^3$ .......................... C09K 3/34; G02F 1/13
[52] U.S. Cl. ...................... 252/299; 73/356; 252/408; 350/346; 350/350 R; 350/351; 560/102; 350/350 S
[58] Field of Search ............. 252/299, 408; 350/346, 350/350 R, 350 S, 351; 73/356; 560/102

[56] References Cited
U.S. PATENT DOCUMENTS

| | | |
|---|---|---|
| 4,017,416 | 4/1977 | Inukai et al. ............ 252/299 |
| 4,032,219 | 6/1977 | Constant et al. ......... 252/299 |
| 4,065,489 | 12/1977 | Steinstrasser et al. ... 252/299 |
| 4,077,260 | 3/1978 | Gray et al. ............... 252/299 |
| 4,082,428 | 4/1978 | Hsu ......................... 252/299 |
| 4,083,797 | 4/1979 | Oh ........................... 252/299 |
| 4,113,647 | 9/1978 | Coates et al. ............ 252/299 |
| 4,136,053 | 1/1979 | Steinstrasser et al. ... 252/299 |
| 4,137,192 | 1/1979 | Matsufuji ................. 252/299 |
| 4,149,413 | 4/1979 | Gray et al. ............... 252/299 |
| 4,195,916 | 4/1980 | Coates et al. ............ 252/299 |

OTHER PUBLICATIONS

Gray, G. W., et al., Mol. Cryst. Liq. Cryst., vol. 34, (Letters), pp. 211–217, (1977).
Goodby, J. W., et al., Mol. Cryst. Liq. Cryst., vol. 34, (Letters), pp. 183–188, (1977).
Gray, G. W., et al., "Liquid Crystals & Plastic Crystals", vol. 1, John Wiley & Sons, Inc., N.Y., N.Y. pp. 104–152, (1974).
Gray, G. W., et al., Electronics Letters, vol. 11, No. 23, pp. 556–557, (1975).
Klanderman, B. H., et al., J. Am. Chem. Soc., vol. 97, No. 6, pp. 1585–1586, (1975).
Gray, G. W., et al., Mol. Cryst. Liq. Cryst., vol. 37, pp. 157–188, (1976).
Gray, G. W., et al., Mol. Cryst. Liq. Cryst., vol. 37, pp. 189–211, (1976).

*Primary Examiner*—Teddy S. Gron
*Attorney, Agent, or Firm*—Stevens, Davis, Miller & Mosher

[57] ABSTRACT

Liquid crystal materials are provided which are esters having the general formula:

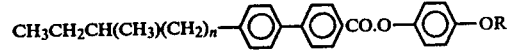

where n has the value 1, 2 or 3 and R is a normal or branched chain alkyl containing up to ten carbon atoms and preferably four to ten carbon atoms.

These materials display a cholesteric mesophase and also a chiral smectic C mesophase underlying the cholesteric mesophase. Both of these mesophases are thermochromic.

19 Claims, No Drawings

LIQUID CRYSTAL MATERIALS

This is a Continuation of application Ser. No. 948,774 filed Oct. 5, 1978, now abandoned, which in turn is a continuation of application Ser. No. 822,342 filed Aug. 5, 1977, now abandoned.

The present invention is concerned with biphenyl carboxylic acid esters which exhibit liquid crystal phases, and with electro-optic display devices incorporating such materials.

Liquid crystal phases are exhibited by certain organic compounds and constitute an intermediate state which exists between the crystalline solid and the fully disordered liquid phase and within which certain long range ordering of the molecules takes place.

There are two broad types of liquid crystal phase; the smectic mesophase in which the long range ordering is of a substantially lamellar type and the nematic mesophase in which the ordering is substantially linear; ie the molecules tend to line up with the long axes of the molecules parallel. Included sometimes as a sub-class of the nematic mesophase and sometimes classified as a separate mesophase is the cholesteric mesophase. This last has a helical long range order imposed upon the linear order of the nematic mesophase. Compounds displaying a cholesteric mesophase are optically active (chiral) and the pitch of the helical twist is determined by the nature and extent of the optical activity. The pitch of the helical twist may be such that thin films of the cholesteric phase reflect visible light, resulting in the observation of bright colours, and the pitch may also be sharply temperature dependent resulting in the reflection of particular colours over particular temperature ranges so that the cholesteric mesophase in question can act as a "thermometer". This behaviour is known as thermochromism.

In accordance with the present invention a liquid crystal material is an ester which has the general formula:

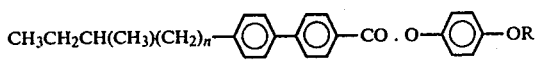

$CH_3CH_2CH(CH_3)(CH_2)_n$—⟨◯⟩—⟨◯⟩—CO.O—⟨◯⟩—OR wherein n has the value 1, 2, or 3, where R is a normal or branched chain alkyl group containing up to ten carbon atoms which may also contain a chiral centre. The alkyl group R is preferably a normal chain alkyl group containing four to ten carbon atoms.

These compounds exhibit a cholesteric mesophase (hereinafter designated Ch) because of their molecular shape and optical activity and also a chiral smectic C mesophase (hereinafter designated $S_C$) underlying the cholesteric mesophase. They exhibit, either on their own or when mixed with one or more compounds capable of forming $S_C$ liquid crystal phases, a chiral $S_C$ liquid crystal phase in which the molecules lie tilted in the smectic layers which are themselves superimposed one upon the other to give a helical distribution of the tilt angles on passing through a stack of layers. A unique feature of the chiral $S_C$ phases of the compounds of the present invention is that, in their planar $S_C$ textures, these mesophases have a helical pitch which gives a selective reflection of coloured light of specific wavelengths which are dependent on temperature, ie, the compounds are thermochromic.

Also, above the $S_C$-Ch transition, the compounds of the present invention exhibit, either on their own or when mixed with one or more other liquid crystal compounds, a cholesteric liquid crystal phase in which the molecules are arranged in the helical formation of that phase such that a film of the phase in the Grandjean plane texture rotates the plane of polarisation of incident polarised light and reflects elliptically polarised light of specific wavelengths when illuminated by ordinary light, so that the mesophases are thermochromic.

The compounds of the present invention have properties such that they may be used in a liquid crystal electro-optic device such as a 'phase change' device in which the material is changed between a so-called 'focal-conic' cholesteric state, which scatters light, and a transparent nematic state by an applied electric field and in accordance with one aspect of the present invention an electrooptic device includes in its liquid crystalline material a compound as hereinbefore defined. It will of course be realised that there may be present, a mixture (solution) of compounds as hereinbefore defined and that other compounds exhibiting liquid crystalline behaviour may be included. Preferably the mixture of compounds used in a eutectic. The optical effect of the electrooptical device may be enhanced by the inclusion of pleochroic dyes. Suitable pleochroic dyes for this purpose are described in Copending UK patent applications numbered 25843/75 and 25859/75.

In accordance with a second aspect of the present invention an electro-optic display device includes as its liquid crystalline material a wide range chiral $S_C$ phase composed of a mixture (solution) of the compounds hereinbefore defined such that the selectively light reflecting (ie coloured) chiral $S_C$ phase is converted to a non-light reflecting, homeotropic (colourless) condition by an applied electric field. That is to say the pitch of the $S_C$ planar structure is effectively unwound by an external electric field which changes the tilt orientation of molecules such that they finally adopt an orthogonal orientation with respect to the layers.

Compounds of the present invention exhibit both a chiral $S_C$ phase and a Ch phase at higher temperatures and mixtures of such materials may exhibit thermochromism in both mesophases. This occurs, it is believed, because the helical pitch lengths of the molecular formations are such as to give strongly temperature dependent Bragg reflection of particular wavelengths of light in the visible spectral region. That is, the materials appear coloured with a colour which varies with the temperature of the material. The sequence of colours given with changing temperature in one direction by the cholesteric phase is the reverse of that given by the chiral $S_C$ phase. The materials of the present invention and mixtures thereof may thus be used in surface thermography, eg, for the detection of breast cancer.

This last mentioned property may be used to produce a temperature sensitive display device, eg, a thermometer giving a visual display resulting from the effect of temperature upon the helical pitch of the material.

The present invention will now be described by way of example only with reference to following Examples which illustrate typical synthetic routes for the preparation of materials in accordance with the present invention.

In the following description of this specification the following symbols are used (+): which refers to an optically active material having a positive optical rotation angle (−): which refers to an optically active material having a negative optical rotation angle $[\alpha]_D^{20}$ which is an absolute measure of the rotatory power (specific rotation) of an optically active material when forming a 10% w/v solution in chloroform.

EXAMPLE 1

This describes the production of (+)-4-(2″-methylbutyl)biphenyl-4′-carboxylic acid by the following route:

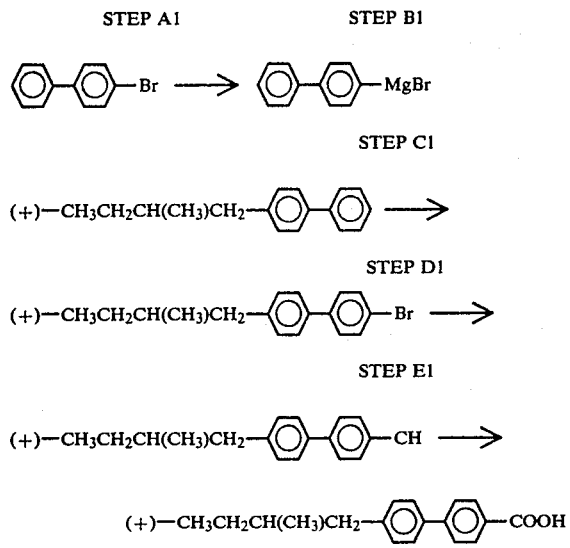

Step A1: The production of biphenylyl-4-magnesium bromide by the 'entrainment' method.

(+)-2-Methylbutyl bromide (0.07 mol), prepared as in Step A3 of example 3, in dry tetrahydrofuran (20 ml), is added to magnesium turnings (0.2 g atom) in dry tetrahydrofuran (20 ml) and the mixture is stirred for 0.5 hours. The reaction is controlled by adding the alkyl bromide in drops.

4-Bromobiphenyl (0.13 mol) in dry tetrahydrofuran (20 ml) is then added in drops so as to maintain a steady refluxing of the solvent. When the addition is complete, the reaction mixture is stirred and heated under reflux for 4 hours and then left to stand overnight.

Step B1: The production of (+)-4-(2″-methylbutyl) biphenyl.

The solution of the Grignard reagent, produced in Step A1, is cooled in an ice bath and, with vigorous stirring, a solution of ferric chloride (0.005 mol) in dry tetrahydrofuran (1.5 ml) is added in drops followed by a solution of (+)-2methylbutyl bromide (0.2 mol) in dry tetrahydrofuran (20 ml). The mixture is stirred for 12 hours, then stirred and heated under reflux for 12 hours. After cooling, the mixture is poured into a beaker containing ice (200 g), water (400 ml) and concentrated hydrochloric acid (40 ml), and stirred for 0.5 hours.

The aqueous mixture is shaken with ether (4×200 ml) and the combined extracts are washed with water (3×100 ml) before drying over anhydrous sodium sulphate. The solvent is evaporated off and the crude oily product is purified using a silica gel column, eluting this with petroleum ether, b.p. 40°–60°. The purified product is then distilled at 0.1 mm Hg pressure.

Step C1: The production of (+)-4-(2″-methylbutyl)-4′-bromobiphenyl.

Under anhydrous conditions, a solution of bromine (0.5 ml) in dry chloroform (5 ml) is added to (+)-4-(2′-methylbutyl) biphenyl (0.04 mol), produced in step B1, dissolved in dry chloroform (10 ml). The reaction mixture is kept at 0° C. throughout the reaction time and light is excluded from the reaction vessel.

After 18 hours and 36 hours two further additions (2×4 ml) of the chloroform solution of bromine (10% v/v) are added.

18 hours after the second addition, the mixture is poured into a sodium metabisulphite solution (150 ml). The aqueous solution is shaken with ether (3×80 ml). The combined extracts are washed with water (3×50 ml), dried over anhydrous sodium sulphate and the solvent evaporated off. The crude solid is recrystallised from ethanol to a constant melting point Step D1: The production of (+)-4-(2″-methylbutyl)-4′-cyanobiphenyl This reaction, which is a conventional synthetic organic chemical reaction, is carried out in a manner analogous to step F2 in Example 2 below.

Step E1: The production of (+)-4-(2″-methylbutyl) biphenyl-4′-carboxylic acid from the corresponding nitrile.

This step may be carried out as follows:

(+)-4-(2″-Methylbutyl)-4′-cyanobiphenyl (0.015 mole), prepared in Step D1, is dissolved in methanol (50 ml) and is added to a mixture of potassium hydroxide (0.54 mole) and sodium hydroxide (0.75 mole) in methanol (40 ml) and water (20 ml). The solution is heated under reflux until evolution of ammonia ceases (ca 72 hr). The mixture is diluted with water (1000 ml) and acidified with concentrated hydrochloric acid. The precipitated product is filtered off and crystallized twice from ethanol: crystal—cholesteric liquid crystal, 224° C., cholesteric liquid crystal—isotropic liquid, 247.4° C.

EXAMPLE 2

The preparation of (+)-4-(3″-methylpentyl)-4′ carboxylic acid by the following route:

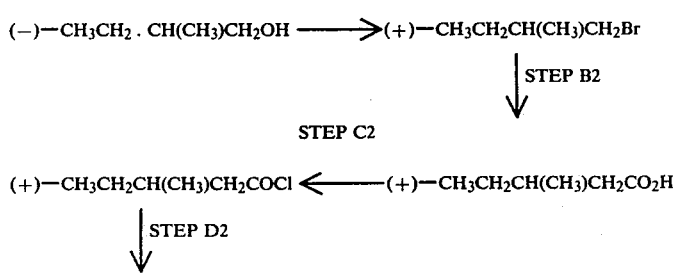

STEP E2

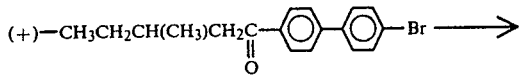

STEP F2

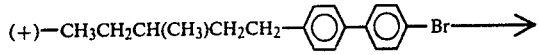

STEP G2

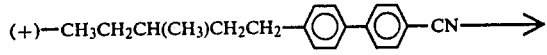

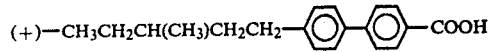

Step A2: The production of (+)-2-methylbutyl bromide.

To a stirred solution of commercially available (−)-2-methylbutanol (0.34 mol) in dry 'Analar' (Trade Mark) pyridine (0.12 mol) is added in drops phosphorus tribromide (0.135 mol). The temperature during the addition is maintained below 15° C. by cooling the mixture in an ice bath. The white emulsion which forms is stirred at room temperature for 2 hours. After this time the crude bromide is distilled from the emulsion under reduced pressure (300 mm Hg) until the mixture turns orange and 'seeths'.

The crude distillate is taken up in petroleum ether (b.p. 40°/60° C.; 100 ml) and is washed with:
(a) 5% sodium hydroxide solution (3×50 ml);
(b) water (3×50 ml);
(c) 10% sulphuric acid (2×50 ml);
(d) concentrated sulphuric acid (100 ml);
(e) water (2×100 ml).

The solution is dried over anhydrous sodium sulphate and the solvent is then evaporated off. The residue is distilled and the fraction boiling at 121° C. collected (96.5% pure by g.l.c.). The product has $[\alpha]_D^{20}$ 3.9°.

Step B2: The production of (+)-3-methylpentanoic acid.

Under anhydrous reaction conditions, the Grignard reagent from (+)-2-methylbutyl bromide (0.38 mol), produced by Step A2, is prepared by conventional methods. The freshly made reagent is poured onto crushed solid carbon dioxide (450 g) in ether and the mixture is left stirring until a paste forms. The paste is acidified with 50% aqueous hydrochloric acid (240 ml). The combined ether layer and ether extracts of the aqueous layer are extracted with 25% sodium hydroxide solution (3×60 ml). The sodium hydroxide extracts are acidified with concentrated hydrochloric acid and then shaken with ether (4×100 ml). The ether extracts are washed with water (2×50 ml), dried over anhydrous sodium sulphate and the solvent is evaporated off. The residue is distilled under slight vacuum (450 mm Hg) and the fraction boiling at 136° C. is collected $[\alpha]_D^{20}$ 6.4°.

Step C2: The production of (+)-3-methylpentanoyl chloride.

The acid from step B2 is converted to its acid chloride using thionyl chloride according to a standard method. After removal of the excess of thionyl chloride, the residual acid chloride is used in step D2 without further purification.

Step D2: The production of (+)-4-(3″-methylpentanoyl)-4′-bromobiphenyl.

To a mixture of anhydrous aluminium trichloride (0.1 mol) in dry dichloromethane (40 ml) is added in drops a mixture of 4-bromobiphenyl (0.086 mol) and (+)-3-methylpentanoyl chloride (0.1 mol) in dichloromethane (80 ml). The mixture is left stirring for 18 hours. After this time, the mixture is poured into a beaker containing, ice (100 g), water (30 ml) and concentrated hydrochloric acid (50 ml) and left stirring for 0.5 hour. The organic layer is separated off, washed with water (2×40 ml), dried over anhydrous sodium sulphate and the solvent evaporated off. The crude product is then crystallised to constant melting point (97° C.) from ethanol.

Step E2: The production of (+)-4-(3″-methylpentyl)-4′-bromobiphenyl.

To lithium aluminium hydride (0.063 mol) in sodium dried ether (100 ml) are added:
(a) anhydrous aluminium trichloride (0.135 mol) in sodium dried ether (100 ml) and
(b) (+)-4-(3″-methylpentanoyl)-4′-bromobiphenyl (0.0185 mol) in dry chloroform (200 ml) at such a rate that the mixture gently boils.

The reaction mixture is then left stirring and boiling for 18 hours. The excess of lithium aluminium hydride is then destroyed by cautiously adding water to the mixture.

The mixture is then poured into a solution of ice (200 g), water (60 ml) and concentrated hydrochloric acid (100 ml) and left stirring for 0.5 hours.

The organic layer is separated off, washed with water (3×100 ml), dried over anhydrous sodium sulphate and the ether is then evaporated off. The solid product is recrystallised from ethanol to constant melting point (101°–102° C.).

Step F2: The production of (+)-4-(-3″-methylpentyl)-4′-cyanobiphenyl.

A mixture of (+)-4-(3″-methylpentyl-4′-bromobiphenyl (0.03 mol), (the product of step E2), cuprous cyanide (0.03 mol) and N-methylpyrrolidone (38 ml) is heated under reflux and stirred for 2 hours. The cooled reaction mixture is poured into a solution of ferric chloride (12 g) concentrated hydrochloric acid, (5 ml) and water (150 ml), and stirred at 60° C. for 0.5 hour.

The organic material is then taken up in ether; the extract is washed with dilute hydrochloric acid (2×100 ml) and water (3×100 ml), dried over anhydrous sodium sulphate, and the solvent is then evaporated off.

The crude oily product is purified by column chromatography using a silica gel column and eluting with chloroform. The purified product is then distilled at 0.1 mm Hg, at an oil bath temperature of 180° C.

Step G2: The production of (+)-4-(3″-methylpentyl)-biphenyl-4′-carboxylic acid from the corresponding nitrile.

The acid may be prepared and purified by a method analogous to that in Step E1 of Example 1. The colourless crystals have crystal-cholesteric liquid crystal, 219° C., cholesteric liquid crystal—isotropic liquid, 242.2° C.

EXAMPLE 3

The preparation of (+)-4-(4″-methylhexyl)biphenyl-4′-carboxylic acid by the following route:

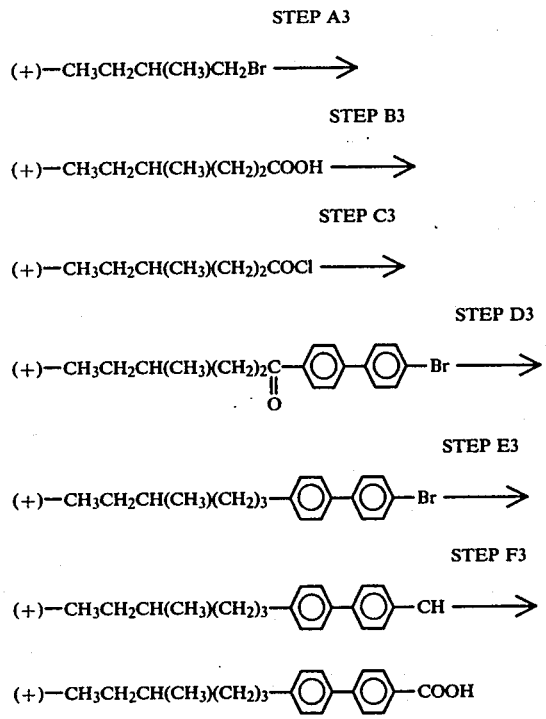

Step A3: The production of (+)-4-methylhexanoic acid.

(+)-2-Methylbutyl bromide, prepared as in step A2 of Example 2 above is converted into (+)-4-methylhexanoic acid by interaction with diethyl malonate followed by hydrolysis of the ester according to a literature method. The product (96% pure by g.l.c.) has an $[\alpha]_D^{20}$ 9.4° and boiled at 134° C. at 25 mm Hg.

Step B4: The production of (+)-4-methylhexanoyl chloride.

The acid from step A3 is converted into the acid chloride by interaction with thionyl chloride according to a standard method. After removal of the excess of thionyl chloride, the residual acid chloride is used in step C3 without further purification.

Step C3: The production of (+)-4-(4″-methylhexanoyl)-4′-bromobiphenyl.

The acid chloride from step B3 is interacted with 4-bromobiphenyl by the method described in step D2 of Example 2. The product is crystallised to constant melting point (56° C.) from ethanol.

The product gives a monotropic smectic phase on cooling the isotropic liquid below the melting point to 28° C.

Step D3: The production of (+)-4-(4″-methylhexyl)-4′-bromobiphenyl.

This compound is prepared by a reduction method analogous to Step E2 of Example 2. The solid product is crystallised to constant melting point (86°-89° C.) from ethanol.

Step E3: The production of (+)-4-(4″-methylhexyl)4′-cyanobiphenyl.

This is prepared and purified by the a method analogous to step F2 of Example 2.

Step F3: The production of (+)-4-(4″-methylhexyl)-biphenyl-4′-carboxylic acid from the corresponding nitrile.

This step may be carried out and the product purified by a method analogous to that of Step E1 of Example 1 to yield a material having the physical constants C-Sc, 175.4° C., So-Ch, 219.1° C., Ch-I, 235.8° C.

EXAMPLE 4

The preparation of 4-alkoyphenols by the following route:

STEP A4

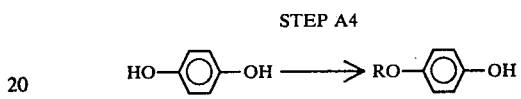

where R is an alkyl group, for example a n-alkyl group.

Step A4: The production of 4-alkoxyphenols illustrated by the preparation of 4-n-octyloxyphenol.

A solution of potassium hydroxide (2.13 mole) in water (238 ml) is added over 30 min to a refluxing mixture of p-quinol (2 moles) and 1-bromo-octane (2.3 moles) in ethanol (640 ml). After heating for an additional 4 hr, the cooled, diluted mixture is shaken with ether (500 ml); the aqueous phase is then acidified. When cold, this is then shaken with chloroform (4×500 ml) and the combined extracts are washed with water (3×200 ml). After drying (Na₂SO₄), the chloroform solution is evaporated, and the residue chromatographed on silica gel using chloroform as eluent. The combined monoether fractions are crystallised from hexane (m.p. 63° C.).

The remaining 4-alkoxyphenols may be prepared by analogous reactions, starting with the appropriate 1-bromo-alkane.

EXAMPLE 5

The production of the biphenyl-4′-carboxylate esters of the present invention by the following route:

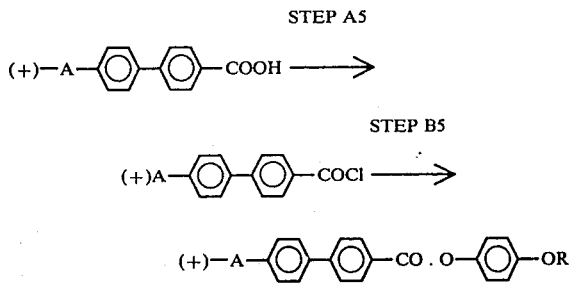

where A and R are as specified above.

Step A5: The production of (+)-4-alkylbiphenyl-4′-carboxylic acid chlorides exemplified by the preparation of (+)-4-(2″-methylbutyl)biphenyl-4′-carboxylic acid chloride.

(+)-4-(2″-methylbutyl)biphenyl-4′-carboxylic acid (0.002 mole), prepared as in Step E1 of Example 1, is heated with thionyl chloride (20 ml) under anhydrous conditions for 1.5 hrs. The excess of thionyl chloride is removed by distillation under reduced pressure. The acid chloride residue is used in the next step without further purification.

Step B5: Production of the ester exemplified by the production of n-heptyloxyphenyl (+)-4-(2″-methylbutyl)biphenyl-4′-carboxylate.

(+)-4-(2″-methylbutyl)biphenyl-4′-carboxylic acid chloride (0.002 mole), prepared in Step A5 above is dissolved in dry 'Analar' pyridine (10 ml) and cooled in an ice bath. 4-n-heptyloxyphenol (0.002 mole), prepared as in Step A4 of Example 4, is added to the stirred solution and the mixture is left, with stirring, for 18 hrs to rise to room temperature. It is then heated at 100° C. for 1 hr. The pyridine is removed by rotary evaporation and the residue column chromatographed on silica gel, eluting with chloroform. The combined fractions of ester are crystallised from hexane.

Analogous esters may be prepared by analogous reactions employing the appropriate starting carboxylic acids and phenols. Physical constants for a series of esters prepared in this way are given in Table 1 below:

TABLE 1
Constants for some compounds of general structure:

| R n=1 | C—Sc or Ch °C. | Sc—Ch °C. | Ch—I °C. | ΔH kcal mol$^{-1}$ |
|---|---|---|---|---|
| n-C$_4$H$_9$ | 81.7 | — | 169.3 | 5.3 |
| n-C$_5$H$_{11}$ | 79.8 | (70) | 164.5 | 6.9 |
| n-C$_6$H$_{13}$ | 68.8 | 80.2 | 163.5 | 5.3 |
| n-C$_7$H$_{15}$ | 80.4 | 87.3 | 157.5 | 7.2 |
| n-C$_8$H$_{17}$ | 76.6 | 88.6 | 155.4 | 10.7 |
| n-C$_9$H$_{19}$ | 79.3 | 89.5 | 147.6 | 10.2 |
| n-C$_{10}$H$_{21}$ | 73.5 | 90.5 | 146.4 | 10.5 |
| n=3 | | | | |
| n-C$_6$H$_{13}$ | 81.0 | 120.3 | 120.3 | — |

The symbols in TABLE 1 above have the following meanings:
C—S$_C$ or Ch
is the crystal to chiral smectic C or cholesteric transition temperature;
S$_C$—Ch
is the chiral smectic C to cholesteric transition temperature;
Ch—I
is the cholesteric to isotropic liquid transition temperature;
ΔH
is the total enthalpy of fusion for the change stable crystal (C) to S$_C$ or Ch liquid crystal phase.
( )
brackets around a temperature indicate a monotropic transition which is not observed during a heating cycle but may be observed on cooling, i.e. the transition is monotropic.

It will be readily apparent to those skilled in the chemical synthetic art that the racemic analogues of all the optically active materials disclosed in Table 1 above may be prepared by methods identical to those hereinbefore disclosed but starting with the racemic reactants.

The data in Table 1 show that none of the pure materials listed exhibits a liquid crystal phase at a low enough temperature to be of direct interest for applications, e.g., at room temperature. However, the compounds are of interest and use in this connection when used as eutectic mixtures with one or with other compatible liquid crystal forming materials, because the mixtures (solutions) then exhibit a cholesteric and/or a chiral S$_C$ phase at much lower temperatures.

In this connection it should be noted that the chiral S$_C$ and Ch phases of any single compound always have the same sense (right or left-handed) of pitch. However, compounds having n even in the group CH$_3$CH$_2$CH(CH$_3$)(CH$_2$)$_n$— have right-handed helical pitch senses, whereas those with odd values n have left-handed helical pitch senses for the S$_C$ and Ch phases.

The following two mixtures are exemplary and the temperatures of the colour changes seen are also recorded.

MIXTURE 1

| Component | Mole fraction |
|---|---|
|  | 0.40 |
|  | 0.31 |
|  | 0.29 | where A is (+)CH$_3$CH$_2$CH(CH$_3$)CH$_2$—

Transition temperatures:
C—S$_C$ - 49° C.
S$_C$—Ch - 72° C.
Ch—I - 163.3°

The colours seen on viewing a thin film of the planar texture of this mixture in a direction at right angles to the film and in reflection are:

| | Temperature (°C.) |
|---|---|
| Selective Reflection | |
| Blue | 50.0 |
| Turquoise | 57.0 |
| Green | 59.0 |
| Yellow | 66.5 |
| Orange | 67.2 |
| Red | 68.5 |
| Transition to cholesteric (S$_C$—Ch) | 72.0 |
| Red | 72.5 |
| Yellow | 72.8 |
| Green | 74.0 |
| Turquoise | 83.0 |
| Blue | 84.5 |
| Selective Reflection | |
| Blue/violet | 92.0 |
| Transition to isotropic liquid | 163.3 |

MIXTURE 2

| Component | Mole fraction |
|---|---|
|  | 0.24 |
|  | 0.16 |
|  | 0.32 |
|  | 0.15 |
|  | 0.07 |
|  | 0.06 |

Transition temperatures:
C—S$_C$ - 39.4° C.
S$_C$—Ch - 74.3° C.
Ch—I - 162.2° C.

The colours seen on viewing a thin film of the planar texture of this mixture in a direction at right angles to the film and in reflection are:

| | Temperature (°C.) |
|---|---|
| Selective Reflection | |
| Red | 39.0 |
| Yellow | 41.0 |
| Green | 43.0 |
| Turquoise | 43.4 |
| Blue | 43.7 |
| Turquoise | 58.7 |
| Green | 60.0 |
| Yellow | 67.0 |
| Red | 69.0 |
| Transition to cholesteric (S$_C$—Ch) | 74.3 |
| Red | 74.5 |
| Yellow | 74.8 |
| Green | 77 |
| Turquoise | 85 |
| Blue | 90 |
| Blue/violet | 97 |
| Transition to isotropic liquid | 162.2 |

The colour changes within the temperature range 39°–43.7° C. constitute a fairly narrow rainbow.

The racemic analogues of the optically active esters disclosed above may also be used as components of eutectic mixtures and this provides a valuable facility for altering the pitch of the chiral phase and therefore the colour which it exhibits without altering the mixture composition.

We claim:

1. A liquid crystal material containing a plurality of compounds at least one of which is a cholesteric liquid crystal compound having a molecular helical pitch length of the order of 0.2 μm, wherein the improvement comprises the said cholesteric compound being an ester having the formula

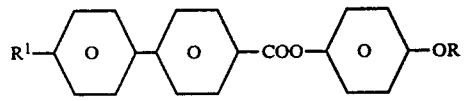

wherein R$^1$ is a branched alkyl group having a chiral center and R is an alkyl group having 1 to 10 carbon atoms with the proviso that the racemates of said at least one cholesteric ester compound are excluded from the liquid crystal material.

2. A liquid crystal material as claimed in claim 1 and wherein R is a straightchain alkyl group containing four to ten carbon atoms.

3. A liquid crystal material as claimed in claim 1 and wherein R$_1$ has a positive optical rotation angle and R is n-butyl.

4. A liquid crystal material as claimed in claim 1 and wherein R$_1$ has a positive optical rotation angle and R is n-pentyl.

5. A liquid crystal material as claimed in claim 1 and wherein R$_1$ has a positive optical rotation angle and R is n-hexyl.

6. A liquid crystal material as claimed in claim 1 and wherein R$_1$ has a positive optical rotation angle and R is n-heptyl.

7. A liquid crystal material as claimed in claim 1 and wherein R$_1$ has a positive optical rotation angle and R is n-octyl.

8. A liquid crystal material as claimed in claim 1 and wherein R$_1$ has a positive optical rotation angle and R is n-nonyl.

9. A liquid crystal material as claimed in claim 1 and wherein R$_1$ has a positive optical rotation angle and R is n-decyl.

10. A liquid crystal material as claimed in claim 1 and wherein R$_1$ is a 4-methylhexyl group which has a positive optical rotation angle and R is n-hexyl.

11. A liquid crystal electro-optic device of the phase change type in which the liquid crystal material is the liquid crystal material of claim 1.

12. A liquid crystal material as claimed in claim 1 and wherein the cholesteric ester compound is produced by the following route:

(i) an optically active halide containing a group R' is converted into an optically active form of

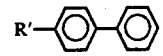

where R' is $CH_3CH_2CH(CH_3)(CH_2)_n$; n = 1, 2 or 3;

(ii)

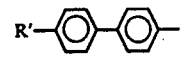

is converted into an optically active form of

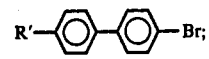

(iii)

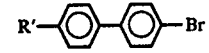

is converted into an optically active form of

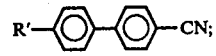

(iv)

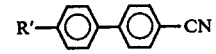

is converted into an optically active form of

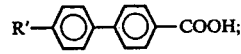

(v)

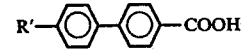

is converted into an optically active form of

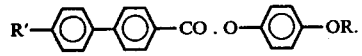

13. A liquid crystal material as claimed in claim 12 and wherein R' is 2-methylbutyl.

14. A liquid crystal material as claimed in claim 1 and wherein the cholesteric ester compound is produced by the following route:

(i) an optically active halide containing a group R" is converted into an optically active form of R"CO.Cl where R" is $CH_3CH_2CH(CH_3)(CH_2)_m$; m=0, 1 or 2;

(ii) R"COCl is converted into an optically active form of

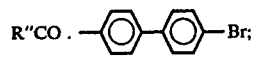

(iii)

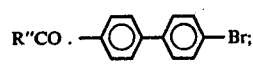

(iv)

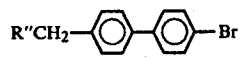

is converted into an optically active form of

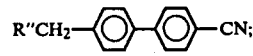

(v)

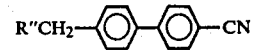

is converted into an optically active form of

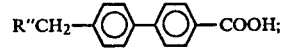

(vi)

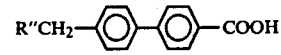

is converted into an optically active form of

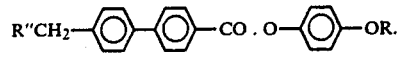

15. A liquid crystal material as claimed in claim 14 and wherein R" is 2-methylbutyl.

16. A liquid crystal material as claimed in claim 14 and wherein R" is 3-methylpentyl.

17. A liquid crystal material as claimed in claim 14 and wherein the conversion of

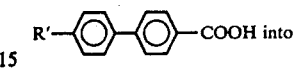

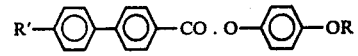

involves producing as an intermediate product the acid chloride

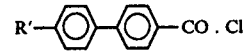

and reacting said acid chloride with a 4-alkoxy phenol

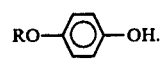

18. A liquid crystal material as claimed in claim 14 and wherein the conversion of $R''CH_2$—⟨◯⟩—⟨◯⟩—COOH into

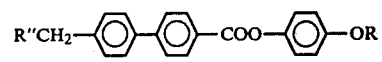

involves producing as an intermediate product the acid chloride

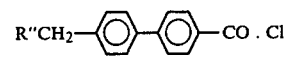

and reacting said acid chloride with a 4-alkoxy phenol

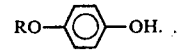

19. A liquid crystal material as claimed in claim 1 and wherein said material itself is cholesteric and has a molecular helical pitch length corresponding to a wavelength region in the visible spectrum for a given temperature.

* * * * *

UNITED STATES PATENT AND TRADEMARK OFFICE
CERTIFICATE OF CORRECTION

PATENT NO. : 4,257,911
DATED : March 24, 1981
INVENTOR(S) : George W. GRAY and Damien G. McDONNELL It is certified that error appears in the above-identified patent and that said Letters Patent are hereby corrected as shown below:

On the title page add the following:

--[30]  Foreign Application Priority Data

August 13, 1976   British 33860--.

Signed and Sealed this

Fourteenth Day of June 1983

[SEAL]

*Attest:*

DONALD J. QUIGG

*Attesting Officer*   *Acting Commissioner of Patents and Trademarks*